US009176027B2

(12) United States Patent
Neyens et al.

(10) Patent No.: US 9,176,027 B2
(45) Date of Patent: Nov. 3, 2015

(54) DEVICE FOR MEASURING PARAMETERS OR FOR TAKING SAMPLES IN MOLTEN IRON OR STEEL

(71) Applicant: Heraeus Electro-Nite International N.V., Houthalen (BE)

(72) Inventors: Guido Jacobus Neyens, Opoeteren (BE); Eric B. Bortels, Lummen (BE); Dries Beyens, Kinrooi (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 270 days.

(21) Appl. No.: 13/653,441

(22) Filed: Oct. 17, 2012

(65) Prior Publication Data
US 2013/0098173 A1  Apr. 25, 2013

(30) Foreign Application Priority Data

Oct. 20, 2011 (DE) .................. 10 2011 116 440

(51) Int. Cl.
*G01N 1/10* (2006.01)
*G01N 1/12* (2006.01)
(Continued)

(52) U.S. Cl.
CPC *G01N 1/125* (2013.01); *B22D 2/00* (2013.01); *G01N 33/1826* (2013.01); *G01N 33/18* (2013.01)

(58) Field of Classification Search
CPC ........ B22D 2/00; B22D 2/001; C21C 5/4673; Y10S 73/09; G01N 1/125; G01N 33/206; G01N 33/18; G01N 33/1826
USPC ......... 73/863.71, 863.81, 864.51, 866.5, 461; 374/140
See application file for complete search history.

(56) References Cited

U.S. PATENT DOCUMENTS 3,656,338 A    4/1972  Collins
4,102,197 A *  7/1978  Bardenheuer et al. ........ 374/140
4,557,152 A * 12/1985  Plessers et al. ............ 73/864.55
(Continued)

FOREIGN PATENT DOCUMENTS

CN    1096369 A    12/1994
CN    2819207 Y     9/2006
(Continued)

OTHER PUBLICATIONS

English translation of an Office Action issued Jun. 5, 2014 in CN Application No. 201210400895.9.
(Continued)

*Primary Examiner* — Peter Macchiarolo
*Assistant Examiner* — Natalie Huls
(74) *Attorney, Agent, or Firm* — Panitch Schwarze Belisario & Nadel LLP

(57) ABSTRACT

A device is provided for measuring parameters or for taking samples in molten iron or steel and for taking samples of slag resting on the melt. The device includes a carrier tube having an immersion end, a lateral circumferential surface, and a measuring head arranged on the immersion end. At least one sensor or inlet opening for a sample chamber present inside the device is arranged at the immersion end of the measuring head. The lateral circumferential surface of the carrier tube or measuring head has an inlet opening extending through an inlet channel to merge in a pre-chamber arranged inside the carrier tube or measuring head. The pre-chamber has, at its end facing away from the immersion end, an entry opening that merges into a slag sample chamber on the side of the pre-chamber facing away from the immersion end.

12 Claims, 3 Drawing Sheets

(51) Int. Cl.
*B22D 2/00* (2006.01)
*G01N 33/18* (2006.01)

(56) References Cited

U.S. PATENT DOCUMENTS

| | | | | |
|---|---|---|---|---|
| 4,565,101 A * | 1/1986 | Boron | ............ | 73/864.57 |
| 4,830,727 A * | 5/1989 | Sasabe et al. | ............ | 204/412 |
| 4,842,418 A | 6/1989 | Conti | | |
| 4,871,263 A * | 10/1989 | Wilson | ............ | 374/139 |
| 5,033,320 A * | 7/1991 | Baerts | ............ | 73/864.59 |
| 5,415,052 A | 5/1995 | Baerts | | |
| 5,515,739 A * | 5/1996 | Baerts | ............ | 73/864.55 |
| 5,577,841 A * | 11/1996 | Wall | ............ | 374/140 |
| 5,584,578 A * | 12/1996 | Clauss, Jr. | ............ | 374/140 |
| 5,720,553 A * | 2/1998 | Falk | ............ | 374/26 |
| 5,979,253 A * | 11/1999 | Knevels et al. | ............ | 73/864.58 |
| 6,142,664 A * | 11/2000 | Ikawa et al. | ............ | 374/140 |
| 6,370,973 B1 * | 4/2002 | Wunsch et al. | ............ | 73/864.53 |
| 6,581,482 B2 * | 6/2003 | Cappa et al. | ............ | 73/864.55 |
| 6,883,392 B2 | 4/2005 | Knevels et al. | | |
| 7,832,294 B2 * | 11/2010 | Neyens | ............ | 73/866.5 |
| 8,001,856 B2 * | 8/2011 | Knevels et al. | ............ | 73/864.56 |
| 8,141,439 B2 * | 3/2012 | Knevels | ............ | 73/864.53 |

FOREIGN PATENT DOCUMENTS

| | | |
|---|---|---|
| DE | 3000201 C2 | 12/1984 |
| DE | 4129930 A1 | 3/1993 |
| DE | 4303687 C1 | 6/1994 |
| DE | 4303688 C3 | 6/2000 |
| DE | 19752743 C5 | 4/2004 |
| DE | 69925388 T2 | 11/2005 |
| DE | 19758595 B4 | 12/2005 |
| EP | 0107219 A1 | 5/1984 |
| EP | 1183513 B1 | 7/2004 |
| JP | S57-154261 U | 9/1982 |
| JP | S63-176410 A | 7/1988 |
| JP | 3011699 U | 5/1995 |
| JP | 2001-525541 A | 12/2001 |
| JP | 2003-240684 A | 8/2003 |

OTHER PUBLICATIONS

English translation of an Office Action issued Jul. 29, 2014 in JP Application No. 2012-231955.
Office Action issued Feb. 14, 2012 in DE Application No. 10 2011 116 440.9.
Office Action issued Apr. 11, 2013 in AU Application No. 2012241071.
Office Action issued Oct. 30, 2014 in KR Application No. 10-2012-0114667.

* cited by examiner

DEVICE FOR MEASURING PARAMETERS OR FOR TAKING SAMPLES IN MOLTEN IRON OR STEEL

BACKGROUND OF THE INVENTION

The invention relates to a device for measuring parameters or for taking samples in molten iron or steel and for taking samples of slag resting on iron or steel melts. The device comprises a carrier tube having an immersion end and a lateral circumferential surface. Arranged on the immersion end of the carrier tube is a measuring head having an immersion end and a lateral circumferential surface. At least one sensor or one inlet opening for a sample chamber present inside the device is arranged at the immersion end of the measuring head.

Devices of this type are known, for example, from German Patent DE 197 58 595 B4. This patent describes devices whose front side has both a thermocouple and an inlet opening for a sample chamber arranged on it. The sample chamber is well-suited for taking slag samples. Moreover, another inlet for a sample chamber, which is well-suited for taking samples of molten metal, is arranged at the front side of the device. Another device that is known from this patent specification comprises a sampler having two lateral inlet openings.

Similar samplers are known, for example, from German Patent DE 197 52 743 C5. Samplers for slag samples are known from European Patent EP 1 183 513 B1 as well. These largely correspond to the samplers already known from DE 197 58 595 B4.

Samplers for molten metal, in which slag and other non-metallic inclusions made of liquid metal sediment, are known, for example, from German published patent application DE 41 29 930 A1 or from U.S. Pat. No. 5,415,052 or U.S. Pat. No. 5,515,739. In this context, contaminants to be separated from the molten metal, when the molten metal flows into the sample chamber, are collected in a pre-chamber situated upstream from the sample chamber for molten metals.

BRIEF SUMMARY OF THE INVENTION

It is an object of the present invention to improve samplers, in particular for taking slag samples, and to provide samples that are of high quality and allow for exact analysis.

This object is achieved by a measuring device of the type described at the outset, characterized in that the lateral circumferential surface of the carrier tube or of the measuring head has a lateral inlet opening arranged on it that extends through an inlet channel to merge in a pre-chamber arranged inside the carrier tube or inside the measuring head, in that the pre-chamber comprises, at its end facing away from the immersion end of the measuring head, an entry opening that merges into a slag sample chamber arranged inside the device on the side of the pre-chamber facing away from the immersion end.

This allows, not only for measuring or sampling at the front side of the device, which is immersed deeply in the molten steel, but also for sampling from a location situated further up at the level of a slag layer resting on the molten metal. In this context, the slag is first guided into a pre-chamber and then into a sample chamber, where the slag rises, since it is more lightweight than the molten steel, and heavier molten metal fractions that may possibly also penetrate into the pre-chamber remain in the pre-chamber. This allows slag samples of high quality to be obtained.

Since the immersion depth and the thickness of the slag layer resting on the molten steel are relatively well known, the depth of penetration of the device can be controlled very accurately in such manner that the front side is arranged in the molten metal, whereas the lateral inlet opening is arranged in the slag layer.

In the immersion probes described herein, a measuring head generally is a separate component arranged at the immersion end of a carrier tube and has sensors or sample chambers arranged on or in it. Measuring heads of this type are, in most cases, essentially made of metal, in particular of steel or foundry sand or cement. In general, carrier tubes are made of cardboard and are attached onto so-called lances, which are operated either automatically or manually and which are used to immerse the carrier tube having the measuring head into the molten mass. The lances are suitable for multiple use, whereas the carrier tubes having the measuring head are spent after a single measurement and need to be replaced.

It is advantageous, in particular, for a metallic splash guard layer to be arranged on the lateral circumferential surface of the carrier tube. The splash guard layer can advantageously be provided to be tube-shaped, whereby it touches in circumferential manner against the external wall of the carrier tube.

Expediently, the splash guard layer can surround the inlet opening arranged on the lateral circumferential surface of the carrier tube without covering or concealing the inlet opening itself. The splash guard layer can have, in particular, a surface area of at least 250 square centimeters that faces away from the carrier tube, i.e. radially outward. This is advantageous, for example, in the case of common carrier tubes having a diameter of approximately 80 millimeters.

The splash guard layer protects the carrier tube material in the immediate vicinity of the inlet opening and thus prevents parts of the carrier tube or combustion products thereof from entering the pre-chamber and then from entering the sample chamber and fouling the sample upon immersion of the carrier tube into the slag layer. This improves the quality of the sample. Preferably, the splash guard layer surrounds the carrier tube from its immersion end to a location above the inlet opening arranged at the lateral circumferential surface of the carrier tube.

The splash guard layer can be relatively thin, for example to have a thickness of approx. 0.5 millimeters. This is advantageous in order for the splash guard layer to protect the carrier tube while the device penetrates into the slag layer, such that high quality filling of the sample chamber with slag is guaranteed. Subsequently, the splash guard layer can expediently dissolve to make the sample chamber containing the sample easier to remove from the device, when the device is pulled out of the molten mass.

It is advantageous for the distance between the immersion end of the measuring head and the inlet opening arranged at the lateral circumferential surface of the carrier tube or of the measuring head to be less than 50 centimeters. Moreover, it is advantageous for this distance to be more than 15 centimeters. The inlet opening arranged on the side is thereby positioned very securely in the slag layer while, concurrently, the depth of penetration of the immersion end of the measuring head in the molten iron or steel is sufficient.

Expediently, the volume of the pre-chamber is larger than the volume of the slag sample chamber, such that the slag is separated to a sufficient degree from the total inflowing material and the slag sample in the sample chamber is of optimal quality. In this context, it can be advantageous for the size of the pre-chamber to be approx. twice the size of the sample chamber. It is also advantageous for the diameter of the inlet opening to the pre-chamber, arranged at the lateral circumferential surface, to be larger than the diameter of the entry opening merging into the slag sample chamber. The inlet opening arranged at the lateral circumferential surface can advantageously be covered by a combustible material, in particular by paper or cardboard.

Moreover, it is advantageous for the slag sample chamber to be bordered by metal plates at its end facing the pre-chamber and at its end facing away from the pre-chamber, since this not only favors the cooling processes of the sample, but also generates a smooth sample surface that can be used for the analysis.

It is also advantageous for the slag sample chamber to be bordered by a wall which is conical in shape between its end facing the pre-chamber and its end facing away from the pre-chamber, since this makes the sample easier to remove from the sample chamber.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
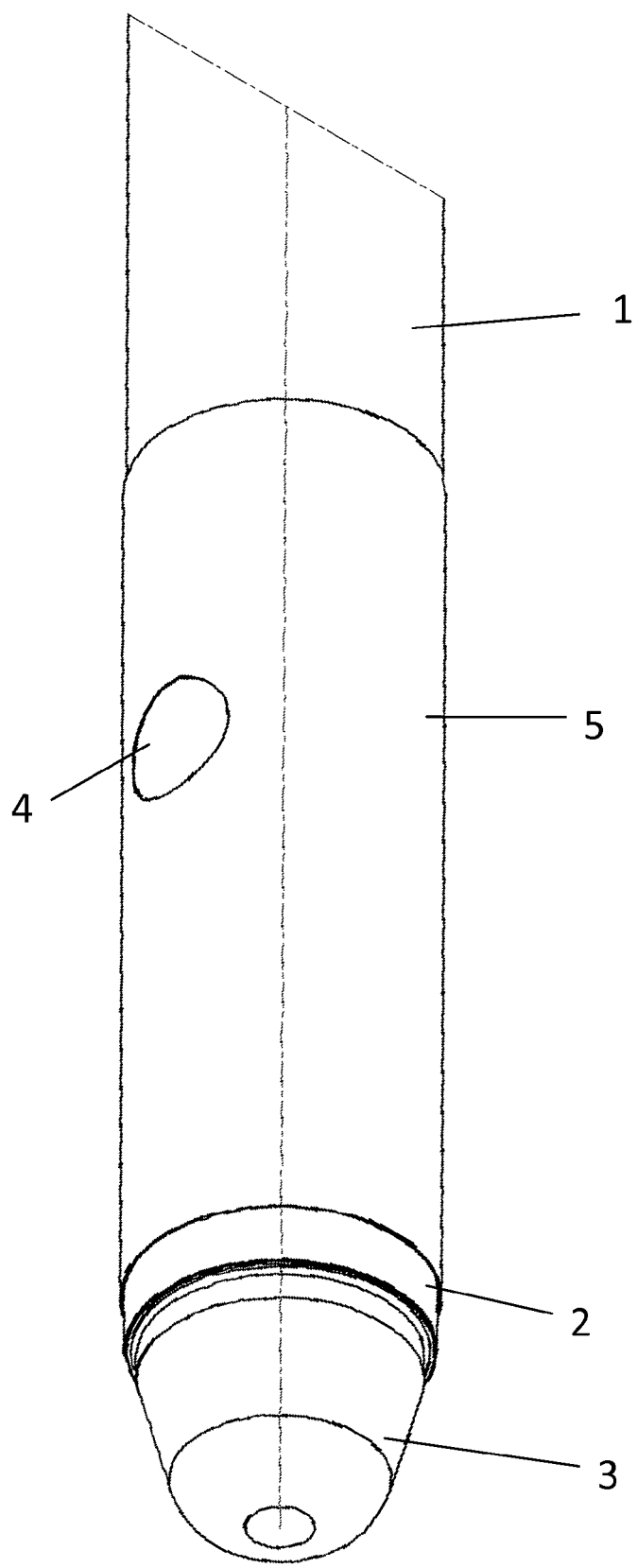
FIG. 1 is a schematic longitudinal perspective view showing the immersion end of a device according to one embodiment of the invention.

The embodiment shown in FIG. 1 is provided with a carrier tube 1 made of cardboard for supporting a measuring head 2. The measuring head 2 is arranged at the immersion end of the carrier tube 1. The measuring head is made of foundry sand or cement. The immersion end of the measuring head is provided with a protective cap 3, which protects the sensors or sample chambers arranged at the measuring head 2 during transport and during immersion through the slag layer. The protective cap 3 is made of steel. Above the measuring head 2, at a distance of approx. 20-25 centimeters from the immersion end (of the protective cap 3), an inlet opening 4 is arranged laterally in the carrier tube 1.

The immersion end of the carrier tube 1 is surrounded by a splash guard layer 5 having a thickness of approx. 0.5 millimeter. The splash guard starts at the measuring head 2 and extends to a location several centimeters above the inlet opening 4. The splash guard layer 5 can be made of steel. The external side of the inlet opening 4 is covered by a layer made of cardboard.

Figure 2:
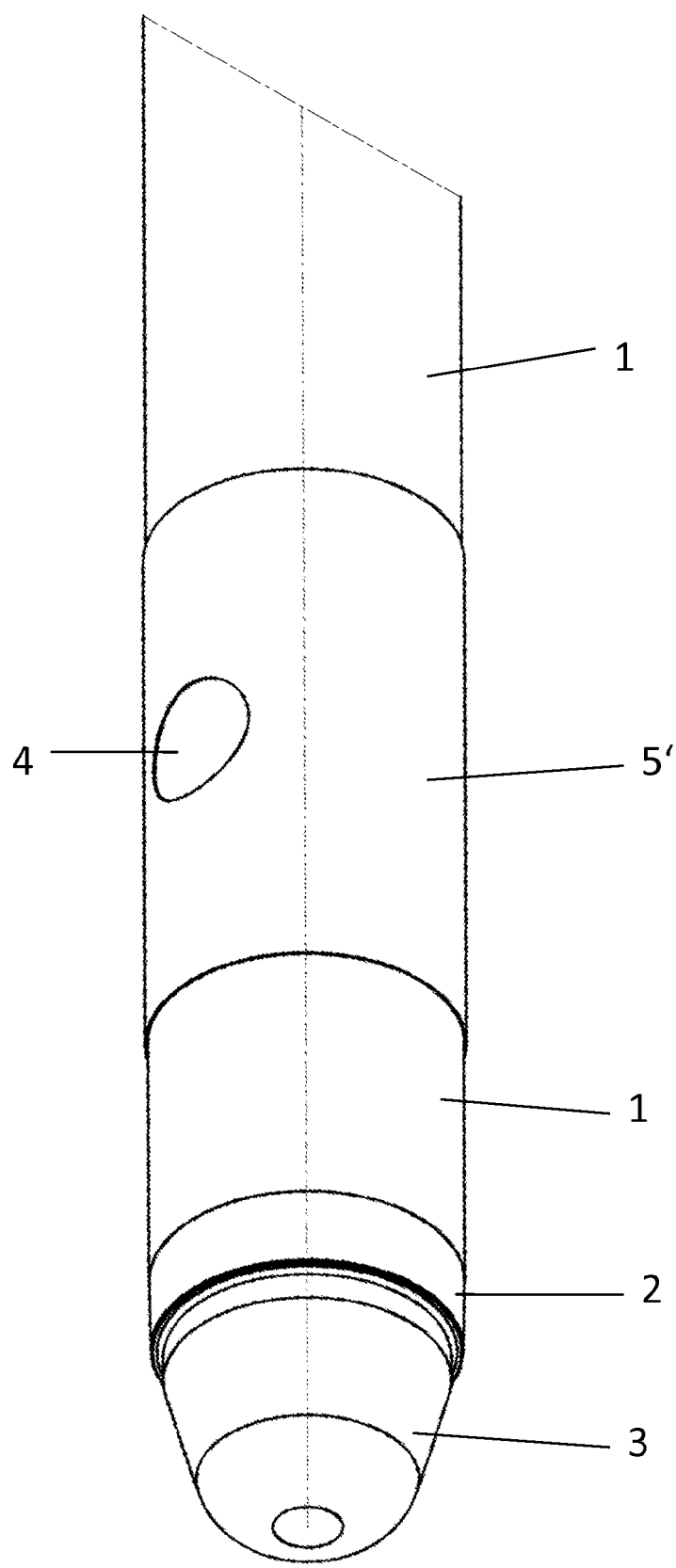
FIG. 2 is a schematic longitudinal perspective view showing the immersion end of a device according to another embodiment of the invention.

FIG. 2 shows a similar arrangement as FIG. 1, wherein the splash guard layer 5' does not start as early as at the immersion end of the carrier tube 1, i.e. right at the measuring head 2, but only several centimeters above, i.e. in front of the inlet opening 4 as seen in the direction of immersion, and extends to a location several centimeters behind the inlet opening 4 on the end facing away from the immersion end.

Figure 3:
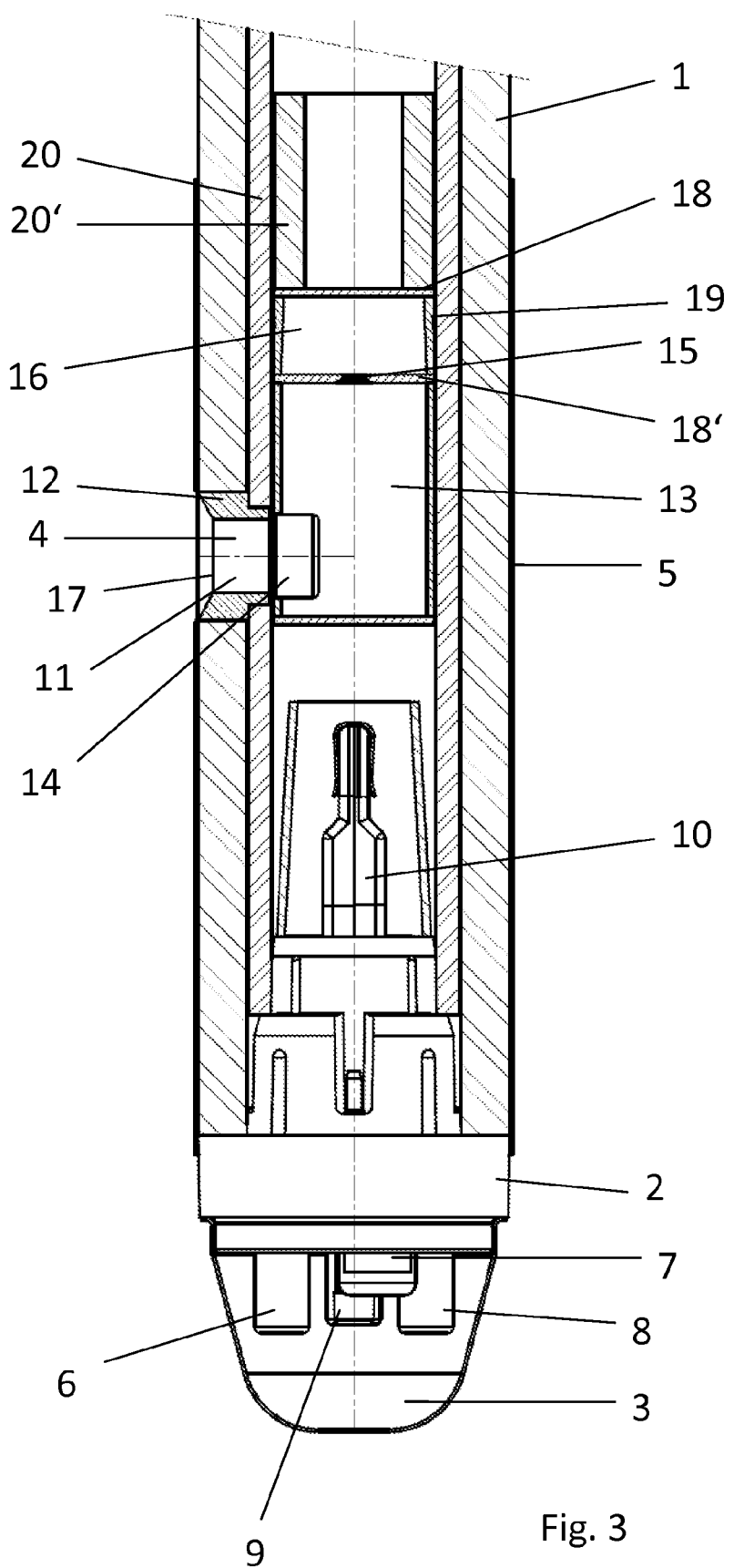
FIG. 3 is a longitudinal sectional view of the immersion end of a device according to an embodiment of the invention.

FIG. 3 shows details of an embodiment of a device according to the invention. An oxygen sensor 6 covered by a protective cap is arranged on the measuring head 2. The oxygen sensor 6 is an electrochemical sensor. The corresponding bath contact 7, as counter-electrode, is also arranged on the measuring head 2. Moreover, the measuring head 2 carries a thermocouple as temperature sensor 8 that is also protected by a cap. Expediently, an inlet opening 9 for a sample chamber 10 for molten metal is arranged at the immersion end of the measuring head 2.

The lateral inlet opening 4 is made of a quartz tube 11 fixed in place in the carrier tube 1 by cement 12. The quartz tube 11 merges into the pre-chamber 13 for slag sampling and is supported there by a metal holder 14. At its end facing away from the immersion end, the pre-chamber 13 comprises an entry opening 15 for the slag sample chamber 16. The inlet opening 4 has a diameter approximately three times the diameter of the entry opening 15. The inlet opening 4 is covered by a cardboard layer 17 that closes the pre-chamber 13 and the slag sample chamber 16 prior to taking the sample and prevents inadvertent ingress of material into the pre-chamber 13 or the slag sample chamber 16.

At its immersion end and at its end facing away from the immersion end, the slag sample chamber 16 is bordered by steel discs 18, 18', and its lateral circumferential surface 19 is also made of steel. The slag sample chamber is provided to be slightly conical in shape to allow the solidified sample to be taken more easily. The diameter of the pre-chamber 13 and the mean diameter of the slag sample chamber 16 are each approximately 35 millimeters, and the pre-chamber 13 has a volume approximately twice the volume of the slag sample chamber 16. The volume of the slag sample chamber 16 is approximately 40 cubic centimeters, such that the weight of the slag sample is 80 grams. Usually, at least 40 grams are needed for a slag analysis.

The inside of the carrier tube 1 has so-called internal cardboard tubes 20, 20' arranged therein, which can be used to fix the slag sample chamber 16, the pre-chamber 13, and other fixtures in place. The device can thus be manufactured relatively easily, and the individual parts can thus be adjusted accurately.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for measuring parameters or for taking samples in molten iron or molten steel and for taking samples of slag resting on the molten iron or molten steel, the device comprising:

a carrier tube having an immersion end and a lateral circumferential surface, the immersion end of the carrier tube having arranged thereon a measuring head having an immersion end and a lateral circumferential surface, the lateral circumferential surface of the carrier tube or of the measuring head having a lateral inlet opening arranged thereon and extending through an inlet channel to merge in a pre-chamber arranged inside the carrier tube or inside the measuring head; and a splash guard layer made of metal and arranged on the exterior of the lateral circumferential surface of the carrier tube or the lateral circumferential surface of the measuring head so as to surround the lateral inlet opening without covering the lateral inlet opening, wherein at least one sensor or one front inlet opening for a sample chamber present inside the device is arranged at the immersion end of the measuring head, and wherein the pre-chamber comprises, at its end facing away from the immersion end of the measuring head, an entry opening that merges into a slag sample chamber arranged inside the device on a side of the pre-chamber facing away from the immersion end of the measuring head.

2. The device according to claim 1, wherein the metallic splash guard layer is tube-shaped.

3. The device according to claim 1, wherein the splash guard layer has a surface area of at least 250 cm$^2$ facing away from the carrier tube.

4. The device according to claim 1, wherein a distance between the immersion end of the measuring head and the lateral inlet opening is less than 50 cm.

5. The device according to claim 1, wherein a distance between the immersion end of the measuring head and the lateral inlet opening is more than 15 cm.

6. The device according to claim 1, wherein a volume of the pre-chamber is larger than a volume of the slag sample chamber.

7. The device according to claim 1, wherein a diameter of the lateral inlet opening is larger than a diameter of the entry opening merging into the slag sample chamber.

8. The device according to claim 1, wherein the lateral inlet opening is covered by a combustible material.

9. The device according to claim 8, wherein the combustible material comprises paper or cardboard.

10. The device according to claim 1, wherein the slag sample chamber is bordered by metal plates at its end facing the pre-chamber and at its end facing away from the pre-chamber.

11. The device according to claim 1, wherein the slag sample chamber is bordered by a lateral wall which is conical in shape between an end of the lateral wall facing the pre-chamber and an end of the lateral wall facing away from the pre-chamber.

12. The device according to claim 1, wherein the splash guard layer is arranged on the exterior of the lateral circumferential surface of the carrier tube to surround at least a portion of the carrier tube.

* * * * *